United States Patent [19]

Oeckl

[11] 4,424,167
[45] Jan. 3, 1984

[54] PROCESS FOR THE PREPARATION OF 2,3-DICHLOROSULPHONYL-ACRYLONITRILES

[75] Inventor: Siegfried Oeckl, Cologne, Fed. Rep. of Germany

[73] Assignee: Bayer Aktiengesellschaft, Leverkusen, Fed. Rep. of Germany

[21] Appl. No.: 315,314

[22] Filed: Oct. 26, 1981

[30] Foreign Application Priority Data

Oct. 31, 1980 [DE] Fed. Rep. of Germany ....... 3041155

[51] Int. Cl.³ .................. C07C 121/30; C07C 121/48; C07C 121/70
[52] U.S. Cl. .............................. 260/465 G; 260/464; 260/465.7
[58] Field of Search .................. 260/464, 465 G, 465.7

[56] References Cited

U.S. PATENT DOCUMENTS

| | | | |
|---|---|---|---|
| 2,298,739 | 10/1942 | Lichty et al. ............. | 260/465.7 |
| 2,384,889 | 9/1945 | Clifford et al. ............ | 260/465.7 |
| 2,385,550 | 9/1945 | Spence ...................... | 260/465.7 |
| 2,437,998 | 3/1948 | Clifford et al. ............ | 260/465.7 |
| 3,078,298 | 2/1963 | Gregory et al. ........... | 260/465.4 |
| 3,140,306 | 7/1964 | Heininger .................. | 260/465.7 X |
| 3,441,614 | 4/1969 | Asscher et al. ............ | 260/465.7 X |
| 3,833,731 | 9/1974 | Grier et al. ................ | 260/465.7 X |
| 4,079,148 | 3/1978 | Oeckl et al. ................ | 260/465.7 X |
| 4,238,405 | 12/1980 | Felix ........................ | 260/465 G X |

FOREIGN PATENT DOCUMENTS

1312 7/1979 European Pat. Off. .
2500265 7/1976 Fed. Rep. of Germany .

OTHER PUBLICATIONS

Achmatowicz, et al., Roczniki Chemii, 30, 243 to 247, (1956).

*Primary Examiner*—Joseph Paul Brust
*Attorney, Agent, or Firm*—Sprung, Horn, Kramer & Woods

[57] ABSTRACT

A process for preparing 2,3-dichlorosulphonyl-acrylonitriles is disclosed by reaction of 3-sulphonyl-propionitriles of the formula $$R^1-SO_2-CH_2-CH_2-CN$$

wherein
 $R^1$ denotes optionally substituted aryl, aralkyl, alkyl or cycloalkyl with a chlorination agent in the presence of a basic catalyst at elevated temperature.

11 Claims, No Drawings

PROCESS FOR THE PREPARATION OF 2,3-DICHLOROSULPHONYL-ACRYLONITRILES

The invention relates to a process for the preparation of 2,3-dichlorsulphonyl-acrylonitriles by chlorination of the corresponding 3-sulphonylpropionitriles.

The preparation of 2,3-dichloro-3-phenylsulphonyl-acrylonitriles by reaction of thiols with trichloro-acrylonitrile and subsequent oxidation to give the corresponding sulphones is known from European Pat. No. 0,001,312. The process described in the above patent is not concerned with the preparation of the unsubstituted 3-phenylsulphonyl-acrylonitrile.

Several complicated reaction steps are required for the preparation of substituted 3-phenylsulphonyl-acrylonitriles according to European Pat. No. 0,001,312.

In contrast, a simple process for the preparation of 2,3-dichlorosulphonyl-acrylonitriles has been found, which is characterized in that 3-sulphonyl-propionitriles of the formula

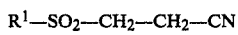

$R^1-SO_2-CH_2-CH_2-CN$ wherein
$R^1$ denotes optionally substituted aryl, aralkyl, alkyl or cycloalkyl,
are reacted with a chlorination agent in the presence of a basic catalyst at elevated temperature.

Straight-chain or branched hydrocarbon radicals with 1 to 12 carbon atoms, preferably lower alkyl radicals (1 to about 6 carbon atoms) may be mentioned as examples of alkyl radicals. Alkyl radicals are, for example, methyl, ethyl, propyl, isopropyl, butyl, isobutyl, pentyl, isopentyl, hexyl, isohexyl, octyl, isooctyl and undecyl. Particularly preferred alkyl radicals are methyl and ethyl.

Aromatic radicals with 6 to 18 carbon atoms are mentioned as examples of aryl radicals, which can optionally be linearly linked with one another or condensed. Phenyl, biphenyl and naphthyl are mentioned as examples. The phenyl radical is particularly preferred.

Radicals with 7 to 14, preferably 7 to 10, carbon atoms are mentioned as examples of aralkyl radicals, in which the aromatic part of the aralkyl can contain 5 to 10, preferably 5 and 6, carbon atoms and the aliphatic part 1 to 6, preferably 1 to 3, carbon atoms. Benzyl, ethylphenyl and α- and β-methyl-naphthyl are mentioned as examples. The benzyl radical is particularly preferred.

Cyclic aliphatic hydrocarbon radicals with 5 to 17 carbon atoms, preferably 5, 6 and 10 carbon atoms, are mentioned as examples of cycloalkyl radicals. It is also possible for several cycloalkyl radicals to be linearly linked with one another or condensed. Cyclopentyl, cyclohexyl and the decalin radical are mentioned as examples. The cyclohexyl radical is a particularly preferred cycloalkyl radical.

The radical $R^1$ can be optionally substituted by radicals which will not be changed in the process of invention. Suitable radicals are lower alkyl ($C_1$ to $C_6$), phenyl and benzyl.

3-Sulphonyl-propionitriles are known from Roczniki Chemii 30, 243 (1956). They can be obtained, for example, by reaction of sulphinic acids or sulphinates with acrylonitrile in aqueous medium.

Preferred 3-sulphonyl-propionitriles are compounds of the formula

$R^2-SO_2-CH_2-CH_2-CN$ wherein $R^2$ denotes optionally substituted phenyl, naphthyl, benzyl, naphthylmethyl, straight-chain or branched lower alkyl or cycloalkyl.

Particularly preferred are 3-sulphonyl-propionitriles of the formula

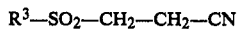

$R^3-SO_2-CH_2-CH_2-CN$ wherein $R^3$ denotes phenyl, 4-chlorophenyl, 2,5-dichlorophenyl, benzyl, methyl, ethyl and cyclohexyl.

The following 3-sulphonyl-propionitriles are mentioned as examples: 3-phenylsulphonyl-propionitrile, 3-methylsulphonyl-propionitrile, (2,5-dichlorophenyl)-sulphonyl-propionitrile and (3-nitrophenyl)-sulphonyl-propionitrile.

Suitable basic catalysts for the process according to the invention are tertiary amines with aliphatic and/or aromatic groups attached to the nitrogen atom, both aliphatic and aromatic groups can be present at one time. The following amines are to be mentioned as examples, such as trimethylamine, triethylamine, dimethylbenzylamine, and dimethylaniline without this signifying any limititations. Those tertiary amines are to be emphasized whose nitrogen atom is a member of a heterocyclic aliphatic or aromatic ring, such as for example N-methylpiperidine, pyridine, α-, β-, or γ-picoline and quinoline. Pyridine is particularly preferred as the basic catalyst.

The quantity of basic catalyst in the reaction mixture can vary within wide ranges. In general, 0.1 to 20% by weight, preferably 1 to 10% by weight, of basic catalyst is employed, relative to the 3-sulphonyl-propionitrile.

The customary chlorination agents, such as elementary chlorine and the phosphorus chlorides, may be mentioned as chlorination agents for the process according to the invention. Chlorine derivatives of sulphur, particularly sulphuryl chloride, may be mentioned as well as chlorination agents preferred chlorination agents for the process according to the invention are the phosphorus chlorides, particularly phosphorus trichloride and phosphorus pentachloride and it can be expedient to employ only a part of the required amount of phosphorus chloride and to chlorinate the already reacted phosphorus pentachloride again by introduction of chlorine.

A chlorination of 3-sulphonyl-propionitriles with chlorine and/or phosphorus chlorides in the presence of pyridine is particularly preferred for the process according to the invention.

The ratio of weight of chlorination agent to basic catalyst can vary in the range from 10:1 to 1:10. However, the 1- to 10-fold amount of the chlorination agent, relative to the pyridine, is preferably employed.

In general, the catalyst is added at the beginning of the chlorination. In some cases, it can be expedient to add basic catalyst additionally during the course of the chlorination.

In general, at least 3 mols of the chlorination agent are employed for the process according to the invention. If, for example, the hydrogen chloride formed entrains a part of the chlorination agents, it can be expedient to employ the latter in excess. Appropriately, 3 to 10, preferably 4 to 5 mols of the chlorination agents, relative to the 3-sulphonyl-propionitrile, are employed for the process according to the invention.

The chlorination agents are metered in such a manner that they react immediately with the product to be chlorinated. In general, an excess of chlorination agent in the reaction medium accelerates the reaction.

The 2,2-dichlorosulphonyl-propionitriles can also be chlorinated in a suitable solvent or diluent, as long as these are inert under the reaction conditions. Those solvents or diluents are suitable in which the reaction components dissolve easily. They include above all the halogen hydrocarbons, such as for example ethylenechloride, carbontetrachloride, chlorobenzene, but also inorganic compounds such as for example, phosphorus oxychloride. However, the process of invention is preferably conducted without any solvent or diluent.

The process according to the invention is carried out at elevated temperatures. It is expedient to select the temperature so that chlorination is sufficiently rapidly effected, without interference from side reactions and decomposition reactions. The process according to the invention is preferably carried out in the temperature range from 30° to 130° C., particularly preferably in the temperature range from 80° to 120° C.

The process according to the invention is customarily carried out under normal pressure. However, it is also possible to carry out the reaction at reduced pressure (for example up to 0.5 bar) or at increased pressure (for example up to 5 bar).

2,2-Dichlorosulphonyl-propionitriles of the formula $$R^1-SO_2-CH_2-\underset{\underset{Cl}{|}}{\overset{\overset{Cl}{|}}{C}}-CN$$

wherein
R$^1$ has the meaning given above,
can occur as intermediate products in the preparation according to the invention of the 2,3-dichlorosulphonyl-acrylonitriles from the 3-sulphonyl-propionitriles. In general, these intermediate products are not isolated and immediately react further to give the 2,3-dichlorosulphonyl-acrylonitriles. Of course, it is however also possible within the scope of the process according to the invention, to employ the 2,2-dichlorosulphonyl-propionitriles instead of the 3-sulphonyl-propionitriles. The 2,2-dichloro-sulphonyl-propionitriles are known, for example, from the German Offenlegungsschrift No. 2,500,265 and can be prepared, for example, by chlorination of 2-chlorosulphonyl-propionitriles.

The process according to the invention can be illustrated, for example, by means of the following equation:

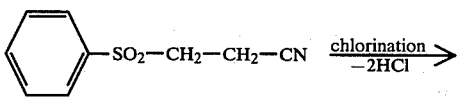

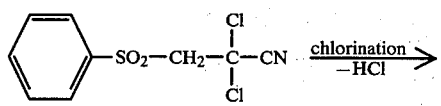

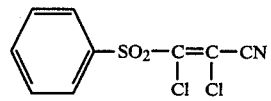

The process according to the invention can be carried out, for example, as follows:

The sulphonyl-propionitriles are warmed up to the reaction temperature, preferably to the temperature at which they are in a molten state. The basic catalyst is then added. About half of the chlorination agent is thereupon introduced rapidly, so that the reaction proceeds at a rapid rate. The further addition of the chlorination agent is preferably introduced at a somewhat lower temperature, according to the progress of the reaction. After termination of the reaction, the reaction mixture is cooled down to room temperature and treated with water. After the aqueous phase is separated off, the 2,3-dichlorosulphonyl-acrylonitrile is obtained from the organic phase.

The 2,3-dichlorosulphonyl-acrylonitrile is produced in high purity by the process according to the invention. Of course, the product according to the invention may be further purified according to customary working up methods, for example by recrystallization from ethanol, in order to achieve higher purity.

It is surprising that, under the conditions according to the invention, the reaction does not stop at the stage of the 2,2-dichlorosulphonyl-propionitriles, but that, on further chlorination, hydrogen chloride is split off and 2,3-dichlorosulphonyl-acrylonitriles are formed.

2,3-Dichlorosulphonyl-acrylonitriles of the formula $$R^1-SO_2-CHCl=CHCl-CN$$

wherein
R$^1$ has the meaning given above,
can be formed by the process according to the invention.

Surprisingly, the new 2,3-dichloro-3-phenylsulphonyl-acrylonitrile can be prepared by the process according to the invention. Particularly the new 2,3-dichloro-3-phenyl-sulphonyl-acrylnitrile is an active compound for combating microorganisms, preferably in industrial materials, especially in non-living things.

2,3-Dichlorosulphonyl-acrylonitriles prepared by the process according to the invention are microbicidal agents, as is known from the European Pat. No. 0,001,312.

EXAMPLE 1

2,3-Dichloro-3-phenylsulphonyl-acrylonitrile 195 g (1 mol) of 3-phenylsulphonyl-propionitrile were melted at 100° C. in a 500 ml four-necked flask and 14 g of PCl$_3$ and 4.2 g of pyridine were added as catalysts. 150 g (2.1 mols) of chlorine at 100° to 90° C. were then introduced during the course of 9 hours. 7 g of PCl$_3$ and 2 g of pyridine were then added once more, and 160 g (2.25 mols) of chlorine was again introduced at 80° C. during the course of 12 hours, a part of the chlorine being entrained with the escaping HCl gas. 200 ml of water were now added dropwise at 20° C., whilst cooling. The phases were separated at 90° C. and the washing operation was repeated with 200 ml of water. In order to eliminate benzenesulphonyl chloride, the mixture was now boiled for 5 hours with 200 ml of water, and the organic phase was separated off and dried in vacuo. 227 g (87%) of a dark brown crude oil was obtained, which solidified on standing overnight. After warming the solid and dissolving it in 50 ml of ethanol, cooling the solution with ice and filtering off the precipitate under suction, 135 g (51%) of pale crystals, melting point 72° C., were obtained.

EXAMPLE 2

2,3-Dichloro-3-methylsulphonyl-acrylonitrile 31 g (0.23 mol) of 3-methylsulphonyl-propionitrile were melted at 100° C. in a 100 ml four-necked flask, and 2.2 g of PCl$_3$ and 0.7 g of pyridine were added. 34 g of chlorine (0.48 mol) were then introduced at 100° C. during the course of 7 hours. After further addition of 1.1 g of PCl$_3$ and 0.4 g of pyridine, 10 g of chlorine were again introduced. After cooling, the reaction mixture was diluted with 30 ml of methylene chloride and extracted twice by shaking with 50 ml of water in each case, and the organic phase was concentrated. 30 g of dark brown oil which, after mixing with a little ethanol, cooling and filtering off under suction, gave 9.5 g (21%) of pale crystals, melting point 110° to 114° C., without the yield of mother liquor.

EXAMPLE 3

2,3-Dichloro-3-(2,5-dichlorophenylsulphonyl)-acrylonitrile 60 g (0.23 mol) of 3-(2,5-dichlorophenylsulphonyl)-propionitrile were melted in a 250 ml four-necked flask at 135° C. 3.2 g of PCl$_3$ and 1 g of pyridine were then added. 49 g (0.69 mol) of chlorine were then introduced at 130° C. during the course of 17.5 hours. According to thin layer chromatography, hardly any starting material was now present. The reaction mixture was now degassed for a short time under vacuum from a water-jet, cooled, and the content of the flask was extracted by shaking with methylene chloride and water, and the organic phase was separated off, dried over Na$_2$SO$_4$ and concentrated. 65 g (85%) of a dark brown viscous oil remained. 50 g (66%) of a pale oil, pure according to analysis, were obtained from the dark brown oil after column chromatography over silica gel. On standing for a relatively long time, crystals of melting point 84° formed.

What is claimed is:

1. A process for the preparation of a 2,3-dichloro-sulphonyl-acrylonitrile which comprises contacting 3-sulphonyl-propionitrile of the formula

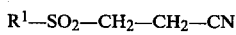
R$^1$—SO$_2$—CH$_2$—CH$_2$—CN wherein
R$^1$ denotes an aryl radical of 6 to 18 carbon atoms, aralkyl radical wherein the aromatic portion contains 5 to 10 carbon atoms and the alkyl portion contains 1 to 6 carbon atoms, alkyl radical of 1 to 12 carbon atoms or cycloalkyl radical of 5 to 17 carbon atoms, each of which radicals can be substituted by a substituent which is not changed in the process with a chlorination agent selected from the group consisting of chlorine, a phosphorus chloride and a chlorine derivative of sulfur in the presenc of a tertiary amine basic catalyst at 30° to 130° C.

2. A process according to claim 1, wherein said basic catalyst is a pyridine base.

3. A process according to claim 2, wherein said basic catalyst is pyridine, picoline or quinoline.

4. A process according to claim 1, wherein said basic catalyst is pyridine.

5. A process according to claim 1, wherein said chlorination agent is a phosphorus chloride.

6. A process according to claim 5, wherein said chlorination agent is phosphorus pentachloride.

7. A process according to claim 1, wherein said chlorination agent is chlorine.

8. A process according to claim 1, wherein said chlorination agent is phosphorus trichloride.

9. A process according to claim 1, wherein said chlorination agent is sulfuryl chloride.

10. A process according to claim 1, wherein said tertiary amine basic catalyst is selected from the group consisting of trimethylamine, triethylamine, dimethylbenzylamine, dimethylaniline, N-methylpiperidine, pyridine, α-picoline, β-picoline, γ-picoline and quinoline.

11. A process for the preparation of a 2,3-dichlorosulphonyl-acrylonitrile which consists essentially of contacting a 3-sulphonyl propionitrile of the formula

R$^1$—SO$_2$—CH$_2$—CH$_2$—CN wherein
R$^1$ denotes an aryl radical of 6 to 18 carbon atoms, an aralkyl radical wherein the aromatic portion contains 5 to 10 carbon atoms and the alkyl portion contains 1 to 6 carbon atoms, an alkyl radical of 1 to 12 carbon atoms or cycloalkyl radical of 5 to 16 carbon atoms, each of which radicals can be substituted by a substituent which does not change in the process with a chlorination agent selected from the group consisting of chlorine, a phosphorus chloride and a chlorine derivative of sulphur in the presence of a tertiary amine basic catalyst at 30° to 130° C.

* * * * *